US010098607B2

(12) United States Patent
Grasruck et al.

(10) Patent No.: US 10,098,607 B2
(45) Date of Patent: Oct. 16, 2018

(54) TOMOGRAPHIC DEVICE AND ALSO METHOD AND COMPUTER PROGRAM FOR MODEL-BASED POSITIONING (71) Applicant: Siemens Aktiengesellschaft, München (DE)

(72) Inventors: Michael Grasruck, Nuremberg (DE); Bernhard Schmidt, Fuerth (DE); Martin Sedlmair, Zirndorf (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 341 days.

(21) Appl. No.: 14/924,792

(22) Filed: Oct. 28, 2015

(65) Prior Publication Data
US 2016/0128666 A1 May 12, 2016

(30) Foreign Application Priority Data
Nov. 12, 2014 (DE) .......................... 10 2014 223 103

(51) Int. Cl.
A61B 6/00 (2006.01)
A61B 6/04 (2006.01)
A61B 6/03 (2006.01)

(52) U.S. Cl.
CPC .............. *A61B 6/582* (2013.01); *A61B 6/032* (2013.01); *A61B 6/0407* (2013.01);
(Continued)

(58) Field of Classification Search
CPC ......... A61B 6/032; A61B 6/466; A61B 6/467; A61B 6/488; A61B 6/54; A61B 6/582;
(Continued)

(56) References Cited

U.S. PATENT DOCUMENTS 5,402,462 A * 3/1995 Nobuta ................ A61B 6/0457
378/20
5,825,843 A * 10/1998 Kobayashi ........... A61B 6/0457
378/20
(Continued)

FOREIGN PATENT DOCUMENTS

CN 1476813 A 2/2004
CN 1589743 A 3/2005
(Continued)

OTHER PUBLICATIONS

Imaging Systems for Medical Diagnostics Arnulf Oppelt p. 540-599 Siemens 2005; 2005.
(Continued)

*Primary Examiner* — Irakli Kiknadze
(74) *Attorney, Agent, or Firm* — Harness, Dickey & Pierce, P.L.C.

(57) ABSTRACT

A tomographic device includes a recording unit with a central system axis, a patient couch movable along the system axis and also a radiation source and a radiation detector interacting with the radiation source. The inventors have recognized that a rapid, precise and reliable positioning of a first recording area can be achieved by the positioning being based on a trained model, wherein the model has been trained with training positions. The tomographic device therefore includes a computing unit, which is designed for calibration of a first position of the first recording area relative to the recording unit based on the trained model. Furthermore the tomographic device includes a control unit for positioning the first recording area in the first position by moving the patient couch relative to the recording unit. The tomographic device is designed for a first tomographic recording of the first recording area in the first position.

24 Claims, 4 Drawing Sheets (52) U.S. Cl.
CPC ............ *A61B 6/0457* (2013.01); *A61B 6/466* (2013.01); *A61B 6/467* (2013.01); *A61B 6/488* (2013.01); *A61B 6/54* (2013.01)

(58) Field of Classification Search
CPC ........... A61B 6/08; A61B 6/463; A61B 6/469; A61B 6/548; A61B 6/583; A61B 6/027; A61B 6/035; A61B 34/20; A61B 6/504; A61B 6/547; A61B 6/587; A61B 6/0407; A61B 6/0457; A61B 2090/376; A61B 2034/2055; A61B 2090/378; A61B 17/1703; A61B 18/1492; A61B 2034/2051; A61B 2090/3782; A61B 2090/3983; A61N 2005/1059; A61N 2005/1063; A61N 5/1049; A61N 2005/1087; A61N 5/1067; A61N 5/1077; A61N 2005/1097; A61N 5/10; A61N 5/107; A61N 5/1082; A61N 5/1081; A61N 2005/1061; A61N 5/1044; A61N 2005/1095; A61N 5/1037; A61N 2005/1054; A61N 5/1043; B60L 11/1818; B60L 11/1825; B60L 2230/16; B60L 11/1803; B60L 11/1814; B60L 11/1816; B60L 11/1877
USPC ................................. 378/4, 18–20, 206–210
See application file for complete search history.

(56) References Cited

U.S. PATENT DOCUMENTS

| | | |
|---|---|---|
| 6,529,762 B1 | 3/2003 | Ladcheck |
| 7,436,927 B2 | 10/2008 | Hempel |
| 2002/0118280 A1 | 8/2002 | Medlar et al. |
| 2003/0225325 A1 | 12/2003 | Kagermeier et al. |
| 2004/0081341 A1 | 4/2004 | Cherek et al. |
| 2004/0082852 A1 | 4/2004 | Cherek et al. |
| 2004/0228453 A1* | 11/2004 | Dobbs .................. A61B 6/463 378/210 |
| 2005/0047553 A1 | 3/2005 | Sembritzki |
| 2005/0256390 A1 | 11/2005 | Laux et al. |
| 2006/0184012 A1 | 8/2006 | Marzendorfer |
| 2007/0172020 A1 | 7/2007 | Nambu |
| 2008/0292048 A1 | 11/2008 | Haras et al. |
| 2009/0285357 A1 | 11/2009 | Khamene et al. |
| 2011/0135190 A1 | 6/2011 | Maad |
| 2011/0188706 A1 | 8/2011 | Zhou |
| 2014/0119500 A1 | 5/2014 | Akahori |
| 2015/0104092 A1 | 4/2015 | Flohr et al. |

FOREIGN PATENT DOCUMENTS

| | | |
|---|---|---|
| CN | 1676096 A | 10/2005 |
| CN | 1792331 A | 6/2006 |
| CN | 101006927 A | 8/2007 |
| CN | 102811769 A | 12/2012 |
| DE | 19943404 A1 | 4/2001 |
| DE | 10109219 A1 | 9/2002 |
| DE | 10210050 A1 | 12/2003 |
| DE | 10232676 A1 | 1/2004 |
| DE | 10232681 A1 | 1/2004 |
| DE | 102006001850 A1 | 8/2007 |
| DE | 102007024452 A1 | 11/2008 |
| DE | 102007017794 B3 | 12/2008 |
| DE | 102012201798 A1 | 8/2013 |
| DE | 102012214513 A1 | 2/2014 |
| DE | 102013220665 A1 | 4/2015 |
| EP | 2420286 A1 | 2/2012 |
| EP | 2596752 A1 | 5/2013 |
| JP | 2013017675 A | 1/2013 |

OTHER PUBLICATIONS

"Automatic computerized radiographic identification of cephalometric landmarks"; Rudolph D. J. et al.; Automatic computerized radiographic identification of cephalometric landmarks; American Journal of Orthodental Dentofacial Orthopedy, 113(2) pp. 173-179, Feb. 1998; 1998.

Sedlmaier Martin et al., "Kontaktlose Oberflächenvermessung zur Topogramm-Optimierung" ; 2013.

German Office Action dated Aug. 25, 2015.

Chinese Office Action and English translation thereof dated Jan. 31, 2018.

* cited by examiner

TOMOGRAPHIC DEVICE AND ALSO METHOD AND COMPUTER PROGRAM FOR MODEL-BASED POSITIONING

PRIORITY STATEMENT

The present application hereby claims priority under 35 U.S.C. § 119 to German patent application number DE 102014223103.5 filed Nov. 12, 2014, the entire contents of which are hereby incorporated herein by reference.

FIELD

At least one embodiment of the invention is directed to a tomographic device, method and/or computer program.

BACKGROUND

Tomography is a method of imaging in which slice images of a three-dimensional recording area are reconstructed. A tomography device has a recording unit with a central system axis. The recording unit can be embodied in a ring shape or in a tunnel shape. The recording unit also has an isocenter, in which the conditions for a tomographic recording are especially advantageous. Typically system axis and isocenter are made to coincide at least partly. The recording area can be moved during the tomographic recording along the system axis and thus through the isocenter. At the end of the tomographic recording the projections are processed in such a way that a tomographic image is produced.

In the case of x-ray tomography x-ray projections are recorded from different projection angles. During this process the recording unit, with a radiation source and also a radiation detector, rotates around the system axis and also around the recording area. The intersection point between the rays emitted by the radiation source and the system axis forms the isocenter of the recording unit. In magnetic resonance tomography the radiation detector can especially be disposed in the form of local coils outside the recording unit. Furthermore in magnetic resonance tomography the system axis is disposed in parallel to a main magnetic field, wherein the isocenter is characterized by an especially homogeneous main magnetic field.

How the recording area is positioned is decisive for the quality of a tomographic image. For example it is regularly desirable to position the radiological focus of the recording area or of an examination area lying in the recording area in the isocenter of the recording unit of a tomography device. The result of this is that the radiation is attenuated as evenly as possible. An exact positioning is especially important in the clinical environment when the recording area involves a region of a patient's body. This is because repeating a tomographic recording as a result of mispositioning involves an additional radiation load and a significant delay in day-to-day clinical procedures. Furthermore a tomographic image of the highest possible quality is indispensible in clinical diagnostics.

Conventionally the patient is positioned by a user moving the patient couch manually. An optical marking, which is projected onto the patient, typically in the form of a laser line, is also used for positioning. A particular problem in such cases is the positioning of the patient perpendicular to the system axis, especially the positioning in the vertical direction. Because of the great time pressure in everyday clinical procedures, the vertical position of the patient in particular is often set only insufficiently accurately.

SUMMARY

An embodiment of the present invention provides a rapid work sequence for a precise and reliable positioning of a patient.

An embodiment of the present invention is directed to a tomographic device, a method and/or a computer program.

Features, advantages or alternate forms of embodiment mentioned here are likewise also to be transferred to the other claimed subject matter and vice versa. In other words the physical claims (which are directed to a device for example) can also be further developed with the features which are described or claimed in conjunction with a method. The corresponding functional features of the method are embodied in such cases by corresponding physical modules, especially by hardware modules.

An embodiment of the invention relates to a tomographic device for model-based positioning. The tomographic device in this case comprises a recording unit with a central system axis, a patient couch able to be moved along the system axis and also a radiation source and a radiation detector interacting with the radiation source. The inventors have recognized that a rapid, precise and reliable positioning of a first recording area can be achieved by the positioning being based on a trained model, wherein the model has been trained with training positions. The training means that the model adapts itself to the habits of a user and especially makes possible an automated positioning. The tomographic device therefore includes a computing unit, which is designed to calibrate a first position of the first recording area relative to the recording unit based on the trained model. The tomographic device further includes a control unit for positioning the first recording area in the first position by moving the patient couch relative to the recording unit, wherein the tomographic device is designed for a first tomographic recording of the first recording area in the first position.

At least one embodiment of the invention further relates to a method for model-based positioning for a tomographic device as well as to a corresponding computer program.

BRIEF DESCRIPTION OF THE DRAWINGS

The invention is described and explained in greater detail below, with reference to exemplary embodiments shown in the figures, in which.

DETAILED DESCRIPTION OF EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An embodiment of the invention relates to a tomographic device for model-based positioning. The tomographic device in this case comprises a recording unit with a central system axis, a patient couch able to be moved along the system axis and also a radiation source and a radiation detector interacting with the radiation source. The inventors have recognized that a rapid, precise and reliable positioning of a first recording area can be achieved by the positioning being based on a trained model, wherein the model has been trained with training positions. The training means that the model adapts itself to the habits of a user and especially makes possible an automated positioning. The tomographic device therefore includes a computing unit, which is designed to calibrate a first position of the first recording area relative to the recording unit based on the trained model. The tomographic device further includes a control unit for positioning the first recording area in the first position by moving the patient couch relative to the recording unit, wherein the tomographic device is designed for a first tomographic recording of the first recording area in the first position.

In accordance with a further embodiment, the model has been trained such that the training positions are each assigned to one of a number of training areas. The training positions can be specified relative to the recording unit. A training area can involve a recording area or an examination area of a patient or of a phantom. Training position and training area can be considered as a pair of values. By training the model with such pairs of values a computing unit based on the model can calibrate the position of a first recording area especially reliably.

In accordance with a further embodiment of the invention, the model is trained such that the training positions are each assigned training information about a radiation absorption, wherein the computing unit is designed for calibration on the basis of first information about the radiation absorption of the first recording area. By taking into account further information during the training, a more precise positioning in respect of the information taken into account can be carried out. It is especially important to take account of the radiation absorption since this decisively influences the image characteristics of the first tomographic recording.

In accordance with a further embodiment of the invention, the first information is based via the radiation absorption on an x-ray recording of the recording area, wherein the x-ray recording involves one of the following variants:
Topogram,
Low-dose spiral recording,
Predecessor of the first tomographic recordings,
Successor to the first tomographic recordings.

This is because, with these variants, the first information about the radiation absorption can be calibrated especially precisely.

In accordance with a further embodiment of the invention, the first position specifies a radiological focal point of the first recording area such that the radiological focal point lies in the isocenter of the recording unit. This aspect relates to a particularly important application of the invention. This is because, when the radiological focal point lies in the isocenter, then the resulting image impression of a tomographic recording is especially homogeneous.

In accordance with a further embodiment of the invention, the first position specifies a geometrical focal point of the first recording area such that the geometrical focal point lies in the isocenter of the recording unit. A further especially important application is involved here. The geometrical focal point is often selected in order to achieve a highest possible local resolution during a tomographic recording.

In accordance with a further embodiment of the invention, the tomographic device comprises an interface for receiving a first 3D image of a patient supported on the patient couch with the first recording area, wherein the model has been trained such that the training positions are each assigned a 3D training image, wherein the computing unit is designed for calibration based on the first 3D image. A 3D training image comprises information about a patient supported on the patient couch. Since depth information about the contour of a patient with the first recording area is also present with the first 3D image, the first position can be calibrated reliably, especially in the vertical direction. Such reliable positioning is as a rule not possible with conventional manual positioning.

In accordance with a further embodiment of the invention, the tomographic device includes a 3D camera, wherein the 3D camera is attached to the tomography device or above the patient couch. In particular the 3D camera can be fastened centrally above the patient couch, on the ceiling of a building for example.

In accordance with a further embodiment of the invention, the tomographic device includes a display for presenting image information based on the first 3D image as well as an input unit for selecting the first recording area in the image information presented. Through the selection of the first recording area in the image information a user can select various recording areas rapidly and flexibly or can correct a recording area once it has been selected. Furthermore the model can be trained with image information based on 3D training images. In such cases the image information based on 3D training images can be shown on the display and the training positions can be selected with the input unit.

In accordance with a further embodiment of the invention, the display and the input unit are embodied together in the form of a touch-sensitive screen, wherein the touch-sensitive screen is designed to present the image information and also to let it be selected by touching the screen. The intuitive handling of a touch-sensitive screen further speeds up the workflow.

At least one embodiment of the invention further relates to a method for model-based positioning for a tomographic device as well as to a corresponding computer program.

A tomography device can involve a magnetic resonance tomography device. In this case the radiation comprises a high-frequency alternating field in the radio-frequency range. The radiation source in this case involves at least one coil for creating the radio-frequency alternating field. The radiation detector in magnetic resonance tomography involves at least one coil for detecting radio-frequency radiation.

Furthermore the tomography device can involve an x-ray device which is designed to record a plurality of x-ray projections from different projection angles. For example such a tomography device involves a computed tomography device with a ring-shaped rotating frame or a C-arm x-ray device. The recordings can be created during an, especially continuous, rotational movement of a recording unit with an x-ray source and an x-ray detector interacting with the x-ray source. In such cases the x-ray source emits x-ray radiation within a fan or cone-shaped area. The x-ray source can especially involve an x-ray tube with a rotary anode. The x-ray detector involves a row detector with a number of rows for example. The x-ray detector can however also be embodied as a flat-panel detector.

The imaging system can have a reconstruction unit for reconstruction of a tomographic image. Furthermore the imaging system can have a computing unit. Both the computing unit and also the reconstruction unit can be embodied both in the form of hardware and also software. For example the computing unit or the reconstruction unit is embodied as an FPGA (acronym for "Field Programmable Gate Array) or includes an arithmetic logic unit.

The model can be embodied in the form of hardware or software and also as an element of the computing unit. If the model is embodied as software it can consist of commands able to be read by a computer. The model is trained with training values, for example training positions. The model can furthermore be trained with pairs of training values, wherein the pairs can for example be given by:
Pair I) Training position—training area,
Pair II) Training position—training information about a radiation absorption, especially of a training area.

Furthermore a training value can relate to the input or selection of a training area. Both a recording area and also a training area can each include an examination area of a patient. An examination area involves head, thorax, abdomen or heart, lungs, bowel for example. The model can also be trained with more than two training values assigned to one another. Such a plurality of training values assigned to one another is referred to below as a multiplet. Thus the training value can relate to information about the desired target position, for example about whether the radiological or the geometrical focal point is to lie in the isocenter. Furthermore the training value can involve the deviation of a training position in relation to a desired target position. A training value can also relate to physical parameters, for example the focal point of a training area or of the patient, or the overall weight of the patient.

The training includes the model establishing a relationship between training values. The model can especially establish a functional association between the training values. When the trained model receives an input value, for example information about the first recording area, it outputs a corresponding function value, for example the first position. The training can involve both supervised training and also unsupervised training or reinforcement training. With supervised training the function value is predetermined. Examples of supervised training are automatic classification or artificial neuronal networks. With unsupervised training the model includes one or more rules which automatically relate the training values to one another, for example by categorization. Examples of unsupervised training are EM algorithms (short for Expectation-Maximization algorithm). Training in the sense of the present application can also be understood as learning, especially machine learning.

A position of a recording area especially relates to the plane perpendicular to the system axis of the recording unit. In specific forms of embodiment of the invention a position of a recording area means a vertical position. A number of positions can be computed for sub-areas of a recording area, in particular the sub-areas can involve slices along the system axis. A position in the isocenter can thus relate to a position for a slice of the patient located in the ray path. Furthermore a specific position can be displayed in a presentation of the patient, for example as a point, as a surface or as a line.

A control unit is used for positioning. The control unit can be embodied both in the form of hardware and also software. In particular the control unit can have modules for calculating and also for sending a control signal, so that the control unit effects the control of the movement of the patient couch with the control signal. A corresponding calibration allows it to be insured that the relationship between the external coordinate system, in which a recording area is located and an internal coordinate system, for example of the 3D camera (and a 3D image) is known to the control unit. The control unit creates the control signal such that the recording area appears at the intended position in the external coordinate system.

The individual steps of the described method can be carried out both automatically and fully automatically. Within the context of the present application "automatically" means that the respective step executes autonomously by way of a computing unit or control unit, and for the respective step essentially no interaction of a user with the imaging system is necessary. In other words the computing activity is carried out for steps such as automatic calibration or automatic positioning by the computing or control unit. The most that the user has to do is to confirm computed results or carry out intermediate steps. In further forms of embodiment of the invention with steps performed "fully automatically" no action at all by a user is needed to carry out these steps. Regardless of whether the individual steps are carried out "automatically" or "fully-automatically", the inventive method can be a component of a workflow, which additionally requires interaction with a user. The interaction with the user can consist of said user manually selecting a recording protocol or a clinical questionnaire, for example from a menu presented by way of a screen.

A recording protocol includes values for recording parameters which define the precise sequence of an, in particular tomographic, recording of an image by way of the tomographic device. Furthermore a recording protocol can include values for recording parameters which influence the subsequent reconstruction of the image. The recording parameters can involve intensity values of the radiation for example.

The geometrical focal point involves a point or an axis which specifies the geometrical center of the recording area. The geometrical center can especially be calibrated based on a homogeneous density distribution of a computed volume or a computed surface of the patient. The radiological focal point involves a point or an axis which specifies the center of the attenuation distribution of the recording area. The radiological focal point can especially be calibrated based on an inhomogeneous density distribution or an inhomogeneous distribution of radiation absorption characteristics of a computed volume or a computed surface of the patient. Radiation absorption in the sense of the present application also includes x-ray scattering. In particular a specific density or a specific radiation absorption characteristic can be assigned to specific part of the body or to an organ of the patient. In such cases generic or theoretically computed radiation absorption characteristics can also be assigned. A scalable patient model, especially in the form of an avatar, can include such an assignment. In this case the patient model can be based on a 3D image of the patient.

The radiological or the geometrical focal point can in such cases especially relate to a radiological or the geometrical focal point averaged along the system axis. In this case, in accordance with a variant, first a characteristic, for example a density distribution or a radiation absorption characteristic, of a recording area can be averaged along the system axis, in order to then calibrate the corresponding focal point. In a further variant a recording area along the system axis is divided into sub-areas, and individual focal points are calibrated for each of these sub-areas, which are then averaged.

A topogram involves an overview recording of a patient, which can especially be recorded from only one projection angle by the recording unit. With a spiral topogram a tomographic x-ray image of the patient is recorded with a low-dose spiral. In a low-dose spiral a far lower x-ray is applied than for recording a tomographic image with a normal spiral. While considerably more than 1 mSv is applied with a normal spiral, with a low-dose spiral less than 200 μSv or less than 100 μSv is applied.

X-ray detectors which extend for an especially long way along the system axis, especially at least 128 rows, can use a part of their detection signals in order to obtain information about the x-ray absorption of a recording area. In particular the detection signals which stem from an edge area relative to the system axis of the x-ray detector can be used. In an x-ray detector with 128 rows these can be rows 1 to 10 or rows 119 to 128 for example. Depending on the edge area from which the detection signals originate, the information about the x-ray information is based on a predecessor or a successor. With a preamble the detection signals stem from an edge area which is less far away from the recording area before the tomographic recording; with a successor the detection signals stem from the edge area which is further away from the recording area before the tomographic recording.

Both the first 3D image and also the 3D training image involve a 3D image. Such a 3D image has spatially three-dimensional image information. In such cases a 3D image includes a spatial two-dimensional image, 2D image for short, wherein the individual pixels of the 2D image are assigned depth information. This depth information thus represents information in a third spatial dimension. A 3D camera is suitable for recording such 3D images. The 3D camera is designed to detect electromagnetic radiation, especially to detect electromagnetic radiation in a low-frequency spectral range compared to x-ray radiation, for example in the visible or infrared spectral range. The 3D camera is embodied for example as a stereo camera or as a runtime measurement system (known as a time-of-flight camera). The 3D camera can also be designed for recording a 3D image by way of structured illumination. An interface is used to receive the 3D image. The interface involves generally-known hardware or software interfaces, e.g. the hardware interfaces PCI-Bus, USB or Firewire.

The screen can involve an LCD, plasma or OLED screen for example. It can also involve a touch-sensitive screen, which is also embodied as an input unit. Such a touch-sensitive screen can be integrated into the tomographic device, for example into a gantry, or can be embodied as part of a mobile device. As an alternative the input unit can be embodied as a keyboard, mouse, microphone for voice input or embodied in some other way.

Figure 1:
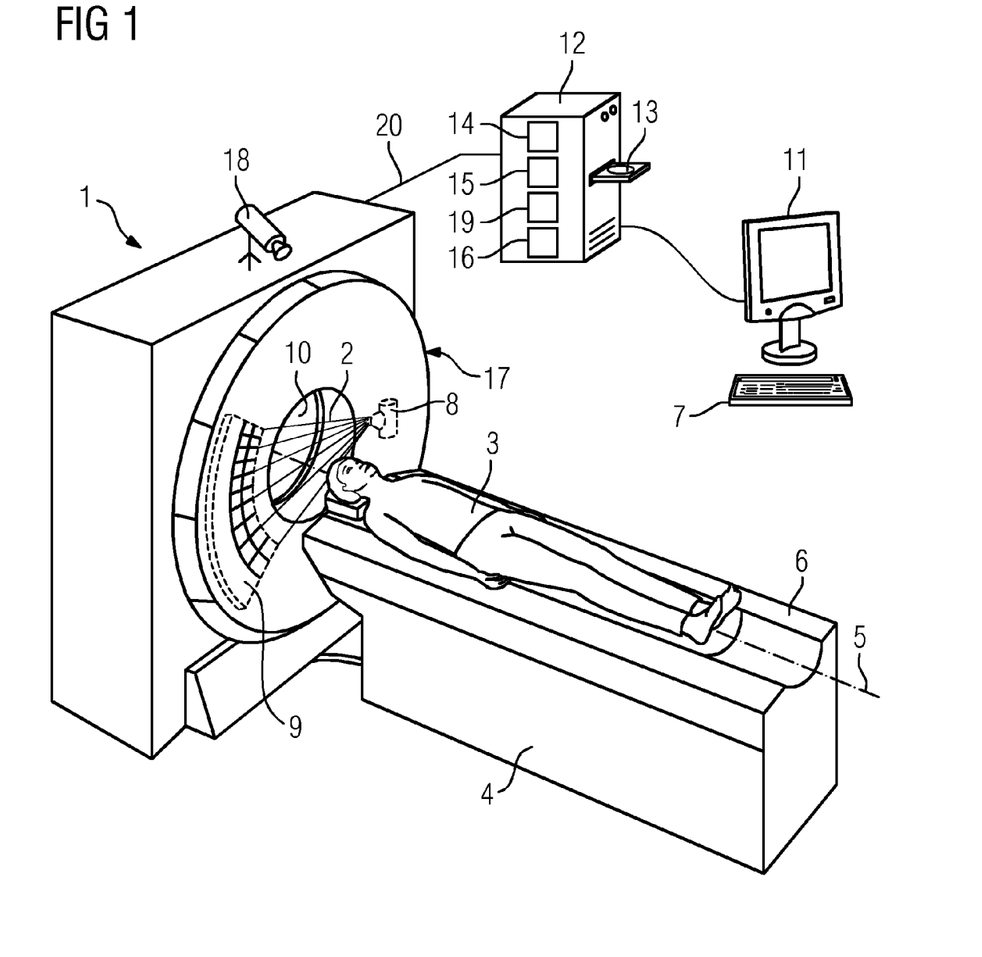
FIG. 1 shows a tomographic device.

FIG. 1 shows a tomographic device using a computed tomography device as an example. The computed tomography device shown here has a recording unit 17, comprising a radiation source 8 in the form of an x-ray source and also a radiation detector 9 in the form of an x-ray detector. The recording unit 17 rotates around a system axis 5 while recording projections, and the x-ray source emits rays 2 during the recording in the form of x-rays. In the example shown here the x-ray source involves an x-ray tube. In the example shown here the x-ray detector involves a row detector with a number of rows.

In the example shown here a patient 3 lies on a patient couch 6 while the projections are being recorded. The patient couch 6 is connected to a couch pedestal 4 so that it carries the patient couch 6 with the patient 3. The patient couch 6 is designed to move the patient 3 along a direction of recording through the opening 10 of the recording unit 17. The direction of recording is generally given by the system axis 5, around which the recording unit 17 rotates during the recording of x-ray projections. In a spiral recording the patient couch 6 is moved continuously through the opening 10 while the recording unit 17 rotates around the patient 3 and records x-ray projections. Thus the x-rays describe a spiral on the surface of the patient 3.

Furthermore the tomographic device shown here has a 3D camera 18, which is equipped with an interface 16 for receiving REC a first 3D image B-1 recorded by the 3D camera 18. In the example shown here the interface 16 is embodied as a part of the computer 12. The computer 12 is connected to an output unit in the form of a display screen 11 and to an input unit 7. The display screen 11 is designed as a screen SCR for displaying various image information based on a 3D image. In particular a photographic image 23 of the patient 3 or a patient model adapted to the patient 3 can be displayed. The input unit 7 is designed to select SEL at least one first recording area A-1. The input unit 7 involves a keyboard, a mouse, a touch-screen or also a microphone for voice input for example.

The calibration CAL of at least one first position P-1 is done by way of a computing unit 15 and also based on a trained model M. The computing unit 15 can include a computer-readable medium 13 or can interact with said medium. In the example shown here a control unit 19 is integrated into the computer 12 and sends a control signal 20 for positioning POS of the patient couch 6. The control signal 20 is sent to a motor for moving the patient couch 6 for example. The couch can be moved along the system axis 5, i.e. horizontally, and also perpendicular to the system axis 5, especially vertically. The movements of the patient couch 6 in different spatial directions can be made independently of one another in such cases.

After or during a tomographic recording a tomographic image based on the recorded projections can be reconstructed. For reconstruction of a tomographic image the imaging system shown here also has a reconstruction unit 14, designed to reconstruct a tomographic image.

Figure 2:
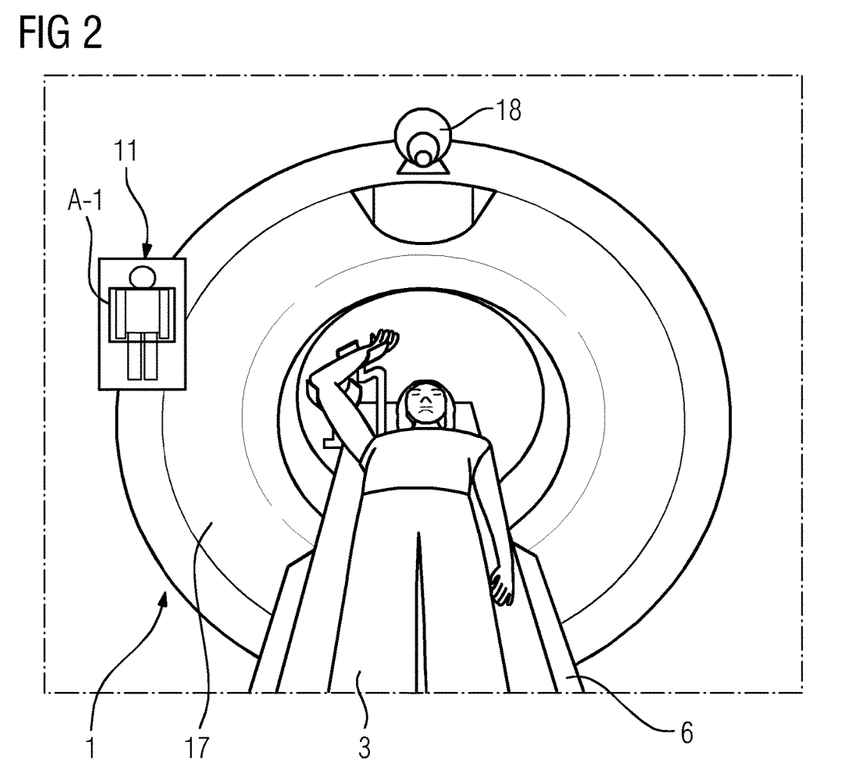
FIG. 2 shows the gantry of a tomographic device with a touch-sensitive screen.

FIG. 2 shows the gantry of a tomographic device with a touch-sensitive screen. In the figure the 3D camera 18 is aligned to the patient couch 6. The touch-sensitive screen 11 can also be connected detachably to the gantry 1. Such a connection can be provided by a holder for a mobile touch-sensitive screen 11, also known as a touch pad. This holder can especially be pivotable. Also shown schematically is the image information as well as a selected first recording area A-1. This first recording area A-1 can be modified by an interaction of a user with the touch-sensitive screen 11. In particular the entire first recording area A-1 together with the first start position S-1 and the first end position E-1 can be shifted. As an alternative the first start position S-1 and the first end position E-1 can also be shifted separately from one another.

Figure 3:
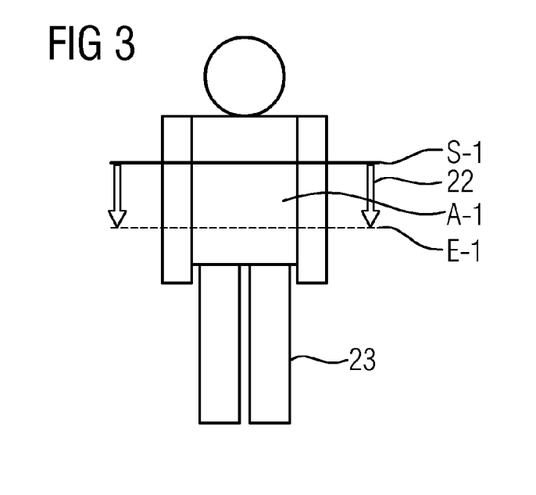
FIG. 3 shows a screen view, with a first recording area, from above

FIG. 3 shows a screen view with a first recording area from above. The image information presented here comprises an image 23 of a patient 3. In the example shown here the first recording area A-1 is represented by a surface highlighted compared to its surroundings. It is delimited by a first start position S-1, represented symbolically by a solid line, and also by a first end position E-1, represented symbolically by a dashed line. Furthermore the recording direction is depicted symbolically, in the example shown here by arrows 22. Based on the selection of the first recording area A-1, a first position P-1 can now be calibrated. In a form of embodiment of the invention the selection SEL is made based on marking of an examination area in the image information. The examination area can furthermore be shown symbolically.

Figure 4:
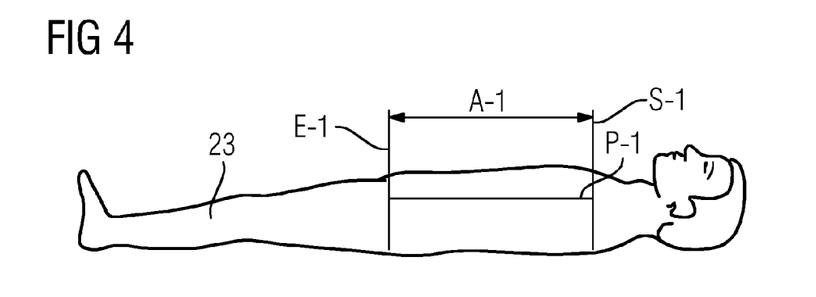
FIG. 4 shows a screen view, with a first recording area, from the side.

FIG. 4 shows a screen view with a first recording area in a side view. The first position P-1 is calibrated CAL on the basis of a trained model M and on the first recording area A-1, wherein the model M has been trained with training positions P-t1 ... P-tn. In this example the first position P-1 involves the radiological focal point of the first recording area A-1. Other forms of embodiment of the invention can involve the geometrical focal point or another focal point respectively.

Figure 5:
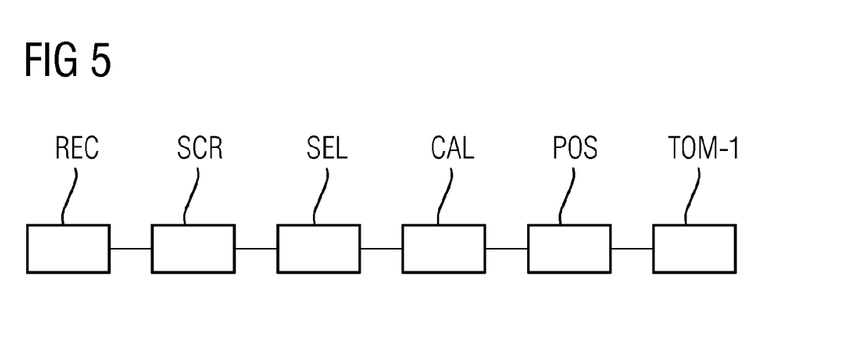
FIG. 5 shows a flow diagram of a method for model-based positioning.

FIG. 5 shows a flow diagram of a method for model-based positioning. It comprises the following steps:
  Calibration CAL of a first position P-1 of a first recording area A-1 relative to a recording unit 17 based on a trained model M and also on the first recording area A-1, wherein the model M has been trained with training positions P-t1 . . . P-tn, Positioning POS the first recording area A-1 in the first position P-1 by moving a patient couch 6 relative to a recording unit 17 with a central system axis 5, First tomographic recording TOM-1 of the first recording area A-1 in the first position P-1 with the recording unit.

In addition the method, as shown here, can also comprise the following steps:

Receiving REC a first 3D image B-1 of a patient 3 supported on the patient couch 6 with the first recording area A-1, wherein the model M has been trained such that the training positions P-t1 . . . P-tn are each assigned to a 3D training image B-t1 . . . B-tn, wherein the computing unit 15 is designed for calibration CAL based on the first 3D image B-1, Display SCR on a screen 11 of image information based on the first 3D image B-1, Selection SEL of the first recording area A-1 in the displayed image information by an input unit 7.

Figure 6:
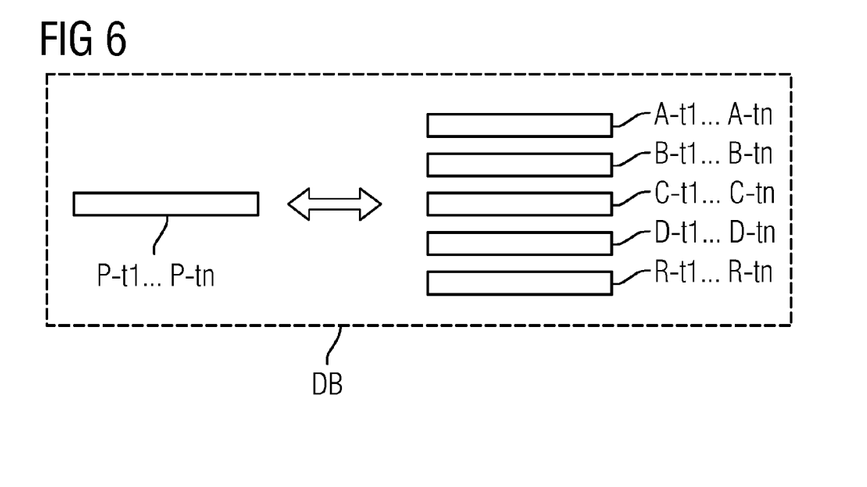
FIG. 6 shows a schematic assignment of training values.

FIG. 6 shows a schematic assignment of training values. In accordance with the invention the first position P-1 is calibrated on the basis of a trained model M, wherein the model M has been trained with training positions P-t1 . . . P-tn. The training positions P-t1 . . . P-tn can especially have been obtained on the basis of a plurality of manual positionings. Typically the training positions are as follows P-t1 . . . P-tn assigned to one of a number of training areas A-t1 . . . A-tn in each case. In this case a training area A-t1 . . . A-tn is assigned precisely to the training P-t1 . . . P-tn which has been calibrated for the respective training area A-t1 . . . A-tn, for example by way of manual positioning. The training areas A-t1 . . . A-tn can correspond to a recording area or to an examination area.

A training position P-t1 . . . P-tn can however also be assigned other training values, for example training information about a radiation absorption R-t1 . . . R-tn. This training information about radiation information R-t1 . . . R-tn can be based on an x-ray recording, wherein the x-ray recording involves one of the following variants:

Topogram, low-dose spiral recording,

Predecessor of the first tomographic recordings TOM-1,

Successor to the first tomographic recordings TOM-1.

Furthermore the model M can be trained such that the training positions P-t1 . . . P-tn are each assigned to a 3D training image B-t1 . . . B-tn, wherein the computing unit 15 is designed for calibration CAL based on the first 3D image B-1. If the recording protocols C-t1 . . . C-tn or recording parameters D-t1 . . . D-tn are acquired during the training in each case, for example by the computing unit 15, a relationship can also be established between the recording protocols C-t1 . . . C-tn and/or the recording parameters D-t1 . . . D-tn and the respective training position P-t1 . . . P-tn. The step of calibration CAL can then be based on a retrievable stored first recording protocol C-1 and/or on a first recording parameter D-1. For example the first recording protocol C-1 and/or the first recording parameter D-1 are selected by a user of the tomographic device. Furthermore the training values can be stored in a database DB. The database DB can be embodied both a component of a computer 12 connected directly to the tomographic device and also a as a component of a server spatially separated from the tomographic device, also referred to as the cloud.

Figure 7:
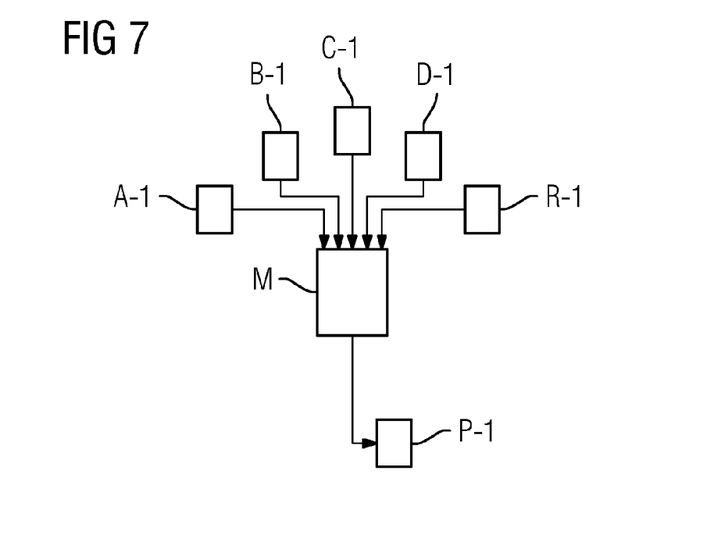
FIG. 7 shows a schematic diagram of how the trained model functions.

FIG. 7 shows a schematic diagram of how the trained model operates. For calibration CAL, the following can be used as input values for the trained model M:

a first recording area A-1 or an examination area, a first image B-1, first information about a radiation absorption R-1 of the first recording area A-1 or the examination area, further information such as for example a first recording protocol C-1 or a first recording parameter D-1.

Just one of these input values can be used for calibration CAL, however a number of input values can also be used. The computing unit 15 then calibrates, based on the model M, the first position P-1 of the first recording area A-1. The trained model M establishes a functional relationship here between the input values and the output in the form of the first position P-1. In a form of embodiment of the invention the first Position P-1 is calibrated on the basis of selected input values. In this case the input values can be selected by a user. In a further form of embodiment, the model M is trained such that different training values are given a different weighting during training. Furthermore this weighting can be selectable, especially by a user. Through this the functional relationship between calibrated input values and the output in the form of the first position P-1 is also weighted.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A tomographic device for model-based positioning comprising:
    a recording unit including a central system axis;
    a patient couch, movable along the central system axis;
    a radiation source and a radiation detector configured to interact with the radiation source;
    a computing unit, designed to calibrate a first position of a first recording area relative to the recording unit based on a trained model, wherein the model has been trained with training positions; and
    a control unit configured to position a first recording area in the first position by moving the patient couch relative to the recording unit, wherein the tomographic device is designed for a first tomographic recording of the first recording area in the first position, wherein the model has been trained such that the training positions are each assigned training information about a radiation absorption, and wherein the computing unit is designed for calibration based on first information about a radiation absorption of the first recording area.

2. The tomographic device of claim 1, wherein the model has been trained such that the training positions are each assigned to one of a number of training areas.

3. The tomographic device of claim 1, wherein the first information about a radiation absorption is based on an x-ray recording of the first recording area, wherein the x-ray recording involves one of the following variants:
    topogram,
    low-dose spiral recording,
    predecessor of the first tomographic recordings, or
    successor to the first tomographic recordings.

4. The tomographic device of claim 1, wherein the first position specifies a radiological focal point of the first recording area such that the radiological focal point lies in an isocenter of the recording unit.

5. The tomographic device of claim 1, wherein the first position specifies a geometrical focal point of the first recording area such that the geometrical focal point lies in an isocenter of the recording unit.

6. A tomographic device for model-based positioning, comprising:
    a recording unit including a central system axis;
    a patient couch, movable along the central system axis;
    a radiation source and a radiation detector configured to interact with the radiation source;
    a computing unit, designed to calibrate a first position of a first recording area relative to the recording unit based on a trained model, wherein the model has been trained with training positions;
    a control unit configured to position a first recording area in the first position by moving the patient couch relative to the recording unit, wherein the tomographic device is designed for a first tomographic recording of the first recording area in the first position; and
    an interface to receive a first 3D image of a patient supported on the patient couch with the first recording area, wherein the model has been trained such that the training positions are each assigned to a 3D training image, and wherein the computing unit is designed for calibration based on the first 3D image.

7. The tomographic device of claim 6, further comprising:
    a 3D camera, wherein the 3D camera is attached to the tomography device or above the patient couch.

8. The tomographic device of claim 7, further comprising:
    a display to screen display image information based on the first 3D image; and
    an input unit for selection of the first recording area in the image information shown.

9. The tomographic device of claim 8, wherein the display and the input unit are embodied together in a form of a touch-sensitive screen, and wherein the touch-sensitive screen is designed to screen display the image information and also to select the information upon being touched.

10. The tomographic device of claim 6, wherein the model has been trained such that the training positions are each assigned training information about a radiation absorption, wherein the computing unit is designed for calibration based on first information about a radiation absorption of the first recording area.

11. The tomographic device of claim 10, wherein the first information about a radiation absorption is based on an x-ray recording of the first recording area, wherein the x-ray recording involves one of the following variants:
    topogram,
    low-dose spiral recording,
    predecessor of the first tomographic recordings, or
    successor to the first tomographic recordings.

12. The tomographic device of claim 6, further comprising:
    a display to screen display image information based on the first 3D image; and
    an input unit to select the first recording area in the image information shown.

13. A method for model-based positioning for a tomographic device including a recording unit with a central system axis, a patient couch movable along the system axis and a radiation source and a radiation detector interacting with the radiation source, the method comprising:

calibrating of a first position a first recording area relative to the recording unit based on a trained model and on the first recording area, wherein the model has been trained with training positions;

positioning the first recording area in the first position by moving a patient couch relative to a recording unit with a central system axis; and first tomographic recording of the first recording area in the first position with the recording unit, wherein the model has been trained such that the training positions are each assigned training information about a radiation absorption, and wherein a computing unit is designed for calibration based on first information about a radiation absorption of the first recording area.

14. The method of claim 13, wherein the model has been trained such that the training positions are each assigned to one of a number of training areas.

15. The method of claim 14, wherein the model has been trained such that the training positions are each assigned training information about a radiation absorption, and wherein a computing unit is designed for calibration based on first information about a radiation absorption of the first recording area.

16. The method of claim 13, wherein the first position specifies a radiological focal point of the first recording area such that the radiological focal point lies in an isocenter of the recording unit.

17. The method of claim 13, wherein the first position specifies a geometrical focal point of the first recording area such that the geometrical focal point lies in an isocenter of the recording unit.

18. A non-transitory computer readable medium, storing a computer program including program segments with commands readable by a computer, configured to perform the method of claim 13 when the computer program is executed in a first computer for controlling a tomographic device.

19. A method for model-based positioning for a tomographic device including a recording unit with a central system axis, a patient couch movable along the system axis and a radiation source and a radiation detector interacting with the radiation source, the method comprising:

calibrating of a first position a first recording area relative to the recording unit based on a trained model and on the first recording area, wherein the model has been trained with training positions:

positioning the first recording area in the first position by moving a patient couch relative to a recording unit with a central system axis; and first tomographic recording of the first recording area in the first position with the recording unit, wherein the first information about a radiation absorption is based on an x-ray recording of the recording area, wherein the x-ray recording involves one of the following variants: topogram, low-dose spiral recording, predecessor of the first tomographic recordings, or successor to the first tomographic recordings.

20. A non-transitory computer readable medium, storing a computer program including program segments with commands readable by a computer, configured to perform the method of claim 19 when the computer program is executed in a first computer for controlling a tomographic device.

21. A method for model-based positioning for a tomographic device including a recording unit with a central system axis, a patient couch movable along the system axis and a radiation source and a radiation detector interacting with the radiation source, the method comprising:

calibrating of a first position a first recording area relative to the recording unit based on a trained model and on the first recording area, wherein the model has been trained with training positions;

positioning the first recording area in the first position by moving a patient couch relative to a recording unit with a central system axis;

first tomographic recording of the first recording area in the first position with the recording unit; and receiving a first 3D image of a patient supported on the patient couch with the first recording area, wherein the model has been trained such that the training positions are each assigned to a 3D training image, and wherein a computing unit is designed for calibration based on the first 3D image.

22. The method of claim 21, further comprising:

displaying, on a screen, of image information based on the first 3D image; and receiving a selection, via an input unit, of the first recording area displayed in the image information.

23. The method of claim 22, wherein the screen and the input unit are embodied together in a form of a touch-sensitive screen, and wherein the screen of the image information and also the selection are carried out by touching the touch-sensitive screen.

24. A non-transitory computer readable medium, storing a computer program including program segments with commands readable by a computer, configured to perform the method of claim 21 when the computer program is executed in a first computer for controlling a tomographic device.

* * * * *

UNITED STATES PATENT AND TRADEMARK OFFICE
CERTIFICATE OF CORRECTION

PATENT NO. : 10,098,607 B2  
APPLICATION NO. : 14/924792  
DATED : October 16, 2018  
INVENTOR(S) : Michael Grasruck et al.

Page 1 of 1

It is certified that error appears in the above-identified patent and that said Letters Patent is hereby corrected as shown below:

In the Claims

Claim 13, Column 17, Line 1, after "position" insert --of--; Claim 19, Column 17, Line 42, after "position" insert --of--; and Claim 21, Column 18, Line 18, after "position" insert --of--.

Signed and Sealed this  
First Day of January, 2019

Andrei Iancu  
*Director of the United States Patent and Trademark Office*